United States Patent [19]

Yoshimura et al.

[11] Patent Number: 4,918,177

[45] Date of Patent: Apr. 17, 1990

[54] SIALIC ACID DERIVATIVES HAVING ACTIVE CARBONYL GROUP

[75] Inventors: Shoji Yoshimura, Iruma; Shohei Shibayama, Tokorozawa; Masaaki Numata, Kawagoe; Masayoshi Ito, Kunitachi; Yoshiyasu Shitori, Tokyo; Tomoya Ogawa, Musashino, all of Japan

[73] Assignee: Mect Corporation, Tokyo, Japan

[21] Appl. No.: 136,144

[22] Filed: Dec. 21, 1987

[51] Int. Cl.[4] .................. C07H 5/04; C07H 15/00; C07G 3/00; A61K 31/715

[52] U.S. Cl. .................. 536/18.7; 536/4.1; 536/17.9; 536/53; 536/18.2; 530/363; 530/322

[58] Field of Search .............. 536/18.7, 17.9, 4.1, 536/17.2, 18.2, 22, 53; 530/363, 322; 514/54

[56] References Cited

U.S. PATENT DOCUMENTS 4,694,076 9/1987 Ogawa et al. .................. 536/18.6
4,797,477 1/1989 Yoshimura et al. .............. 536/18.7

*Primary Examiner*—Ronald W. Griffin
*Assistant Examiner*—Everett White
*Attorney, Agent, or Firm*—Rodman & Rodman

[57] ABSTRACT

A sialic acid derivative having an active carbonyl group represented by the formula [I]:

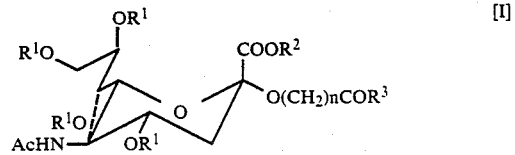

wherein $R^1$ represents hydrogen or acetyl group; $R^2$ represents hydrogen, a metal or a lower alkyl group; $R^3$ represents hydrogen, hydroxyl group, or a residue removed hydrogen from an alcohol portion of an active ester; Ac represents acetyl group; and n is 1 to 20, respectively. This sialic acid derivative [I] can be utilized as a starting material for various complex having a sialic acid in the molecule since it has an active carbonyl group in the molecules so that it shows high reactivity.

36 Claims, No Drawings

SIALIC ACID DERIVATIVES HAVING ACTIVE CARBONYL GROUP

BACKGROUND OF THE INVENTION

(1) Field of the Invention

This invention relates to a novel sialic acid derivative, more specifically to a sialic acid derivative having an active carbonyl group in the molecule, a biological half-life elongating agent for a physiologically active substance using said novel sialic acid derivative, a binder of coupling gel for affinity chromatography and a sialic acid derivative composed of said novel sialic acid derivative combined with various amino compounds such as an amino acid and a protein.

(2) Related Art Statement

It has been known that a neuraminic derivative such as an N-acetylnueraminic acid, i.e., a sialic acid derivative has been present in the animal kingdom or on a cell surface of some bacteria as a sialo-complex (glycoprotein, glycolipid, oligosaccharide and polysaccharaide).

In recent years, the above sialic acid derivative is a compound regarded inportant in medical and pharmaceutical fields such as nervous function, cancer, inflamation, immunity, virus infection, differentiation and hormone receptor, and has attracted attention as a pecular active molecule located on a cell surface.

However, the actual function of the sialic acid derivative in the aforesaid sialic acid complex, still remains a matter of conjucture.

Also, the sialic acid derivative has been researched by many natural organic chemists and various derivatives having simple structure have already been synthesized, but there has been not found a derivative which shows remarkable physiological activity.

SUMMARY OF THE INVENTION

An object of the present invention is to provide a novel sialic acid derivative represented by the formula [I]:

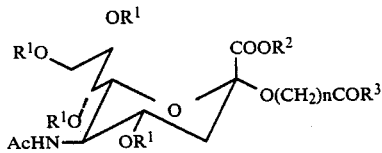

wherein $R^1$ represents hydrogen or acetyl group; $R^2$ represents hydrogen, a metal or a lower alkyl group; $R^3$ represents hydrogen, hydroxyl group, or a residue removed hydrogen from an alcohol portion of an active ester; Ac represents acetyl group; and n is 1 to 20, respectively.

Another object of the present invention is to provide a biological half-life elongating agent of various physiologically active substances utilzing the high reactivity of an active carbonyl group possessed by a sialic acid derivative represented by the above formula [I].

Still snother object of the present invention is to provide a binder of a coupling gel for affinity chromatography utilizing the high reactivity of an active carbonyl group possessed by a sialic acid derivative represented by the above formula [I].

A still further object of the present invention is to provide a novel sialic acid derivative represented by the formula [II]:

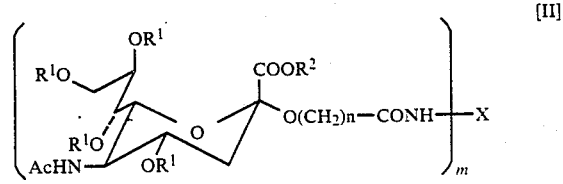

wherein $R^1$ represents hydrogen or acetyl group; $R^2$ represents hydrogen, sodium or a lower alkyl group; Ac represents acetyl group; X represents a residue removed m amino group(s from an amino group; m is 1 to 60; and n is 1 to 20, respectively).

The above and other objects and novel characteristics of the present invention will become more clear by the following detailed description and examples.

DETAILED DESCRIPTION OF THE PREFERRED EMBODIMENTS

The sialic acid derivatrives represented by the above formula [I] are more specifically those having the structure where in place of the COOH group at the C-2 position of N-acetylneuraminic acid represented by the following formula [Ia]:

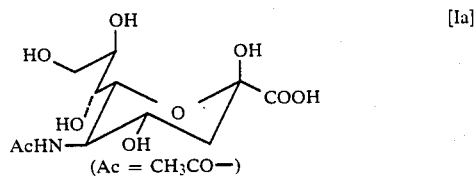

or N-acetylneuraminic acid derivative represented by the formula [Ib]:

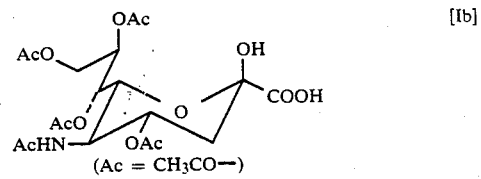

a substituent having an active carbonyl group at terminal such as —O(CH$_2$)$_n$COOH, ester of —O(CH$_2$)$_n$COOH, or —O(CH$_2$)$_n$CHO, is incorporated and further those having the structure where in place of the OH at the C-2 position, —COOH, an ester of —COOH or a metallic salt of —COOH is incorporated.

The sialic acid derivative [I] can be effectively prepared by using alkyl 2-chloro-4,7,8,9-tetra-O-acetyl-5-N-acetylneuraminate represented by the following formula [Ic]:

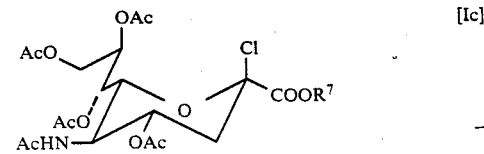

wherein $R^7$ represents a lower alkyl group and Ac represents acetyl group as a starting material.

In one example of preparation the COOH group at the C-2 position of 5-N-acetylneuraminic acid is first esterified in the conventional manner, and after the 4,7,8 and 9 positions are O-acetylated in the conventional manner, replacing the OH group at the C-2 position with chlorine to obtain alkyl 2-chloro-4,7,8,9-tetra-O-acetyl-5-N-acetylneuraminate represented by the above formula [Ic]. The alcohol to be used for esterification is preferably a lower alcohol having no unsaturated bond in the molecule, more preferably methanol.

Next, chlorine is replaced by using an unsaturated alcohol having a double bond in the molecule to introduce an unsaturated alkoxy group, $R^8=CH-(CH_2)_n-O-$ (where $R^8$ represents a alkylidene group) to the C-2 position of the above mentioned N-acetylneuraminate. Here, preferably n is 1 to 20.

While details of this substitution reaction are described in Example 4 below, generally, the compound represented by the following formula [Id] can be obtained by reacting, in a polar solvent such as tetrahydrofuran, the above mentioned N-acetylneuraminate and an unsaturated alcohol represented by the formula $R^8=CH-(CH_2)_n-OH$, where $R^8$ represents a alkylidene group in an inert gas atmosphere such as argon.

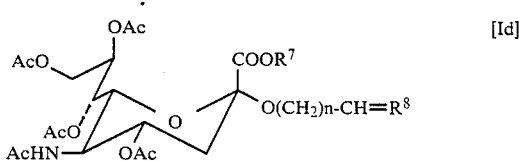

wherein $R^7$ represents a lower alkyl group; $R^8$ represents a alkylidene group and Ac represents acetyl group.

Next, by oxidation of the unsaturated alkoxy group, $R^8=CH-(CH_2)_n-O-$, where $R^8$ represents a alkylidene group, thus introduced, the compound represented by the following formula [Ie] can be obtained.

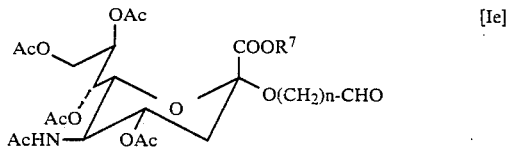

wherein $R^7$ represents a lower alkyl group.

Details of this oxidation reaction are described in Example 1 below, and generally, the above compound [Id] is dissolved in a polar solvent such as dichloromethane and then oxidizing the double bond portion of the unsaturated alkoxyl group by introducing ozonide oxygen under cooling.

After removal of the ozonide oxygen, acetic acid and zinc powder were added to the reaction mixture to react at room temperature to obtain the desired compound.

Also, when the aldehyde group introduced at the terminal of the alkoxy group of the above compound [Ie] is oxidized with potassium permanganate, etc., it is easily converted into a carbonyl group to give the compound represented by the following formula [If]:

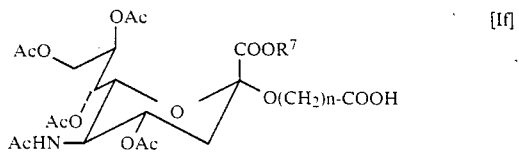

wherein $R^7$ represents a lower alkyl group and Ac represents acetyl group.

When the above compound [Id] is oxidized by using potassium permanganate, etc., it is possible to produce the compound [If] directly, without the above compound [Ie], and details of these oxidizing reactions are described in Example 2 below.

Further, by an esterification reaction of the compound having an OH group and an active carbonyl group in the molecule such as N-hydroxysuccinimide, N-hydroxy-5-norbornene-2,3-dicarboximide or N-hydroxyphthalimide with the above compound [If], other sialic acid derivatives having an active carbonyl group can be obtained.

For example, when the above compound [If] and N-hydroxysuccinimide are esterified in the conventional manner, the compound represented by the following formula [Ig] can be obtained.

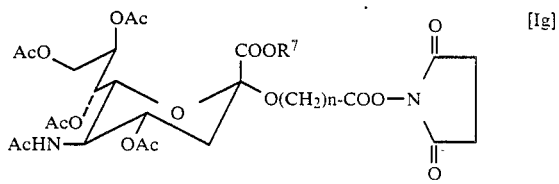

wherein $R^7$ represents a lower alkyl group and Ac represents acetyl group.

Since the sialic acid derivative [I] of the present invention has a carbonyl group such as a carboxyl group or an aldehyde group in the molecule, it shows a high reactivity to other compounds having a functional group capable of reacting with these groups, such as an amino compound, and is an extremely useful compound as a starting material or an intermediate for synthesizing various sialic acid derivatives.

For example, in case where an amino acid is administered to animals or the human body as a nutrient or in the case where ,insulin, growth hormone, interferon or immunogen is administered as a pharmaceutical, if they are administered as a complex combined with the sialic acid derivative [I], it is expected that the biological reaction inherent in the physiologically active substance is inhibited or delayed by the presence of this sialic acid derivative [I]. Therefore, the durability of the above physiologically active substance in the body is heightened, and the valid effect of a medicine can be obtained with a small amount of administration.

The sialic acid derivative [I] is an extremely useful compound as an elongating agent for biological half-life of the above various physiolgically active substances.

Further, when the sialic acid derivative [I] and a matrix of gel support are combined with each other through a spacer composed of an amino compound, the coupling gel for affinity chromatography represented by the following formula [III] can be obtained.

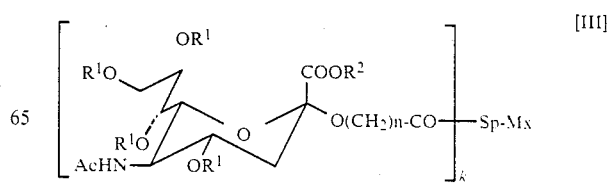

wherein $R^1$ represents hydrogen or acetyl group; $R^2$ represents hydrogen, a metal or a lower alkyl group; Sp represents a residue removed k terminal amino group(s) from the amino compound; Mx represents a gel support; Ac represents acetyl group; n is 1 to 20 and $k \geq 1$.

The above coupling gel for affinity chromatography can elute, after washing out non-binding substances, an objective substance selectively maintaining its activity, since the sialic acid derivatives fixed at the terminals show a specific binding effect to a specific objective substance such as, for example, an antigen. Therefore, it can be utilized for purification of a substance which recognizes the sialic acid or derivatives thereof, such as the above antigen, and the like.

As the spacer composed of the above amino compound, there may be exemplified the compounds having amino group(s) at the terminals such as $H_2N-(CH_2)_6-NH_2$ and $HO-CH_2-CH(OH)-CH_2-NH-(CH_2)_6-NH_2$.

Also, as the matrix of the gel support, there may be exemplified agarose, and the like.

This, the sialic acid derivative [I] is a useful compound for the aforesaid binder of a coupling gel for affinity chromatography.

As the sialic acid derivative particularly preferable for the binder, there may be exemplified, among the above formula [I], those in which the alcohol portion of the active ester is N-hydroxysuccinimide, N-hydroxy-5-norbornene-2,3-dicarboximide, N-hydroxyphthalimide, N-hydroxybenzotriazole, p-nitrophenol, 2,4-dinitrophenol, 2,4,5-trichlorophenol and pentachlorophenol.

Next, the sialic acid derivative represented by the above formula [II] is, more specifically, those in which the sialic acid derivative [I] and an amino compound are bonded to each other via an amido bonding.

As the above amino compound, there may be exemplified various physiologically active substances including a lower molecular weight compound such as a lower amine, an amino acid, etc. and a higher molecular weight compound such as a peptide, a protein, or conjugated protein with which a protein and a prosthetic group are combined.

The aforesaid sialic acid derivative [II] can be effectively produced by using the above sialic acid derivative [I] as the starting material. The preparative methods in which an amino acid or derivatives thereof is used as the amino compound are described in Examples 8 to 12, 15 and 18 mentioned below, while those in which a protein is used as the amino compound are described in Examples 13 to 14 and 17, mentioned below, respectively.

Further, when the amino compound is a lower amine, it can be prepared by utilizing the well known condensation reaction.

It can be expected that the sialic acid derivative [II] has, due to the presence of the sialic acid derivative [I], a function of inhibiting or delaying the biological reaction of the amino compound bonded to the sialic acid derivative [I]. Accordingly, if one wishes to maintain the physiological activity of a physiologically active substance composed of the amino compound in a body, this can be effectively accomplished by administering it in the form of the sialic acid derivative [II].

In the following, preferred embodiments of the present invention will be explained by referring to Examples, but the following Examples are not limitative of the present invention.

EXAMPLE 1

Synthesis of methyl(formylmethyl 5-N-acetyl-3,5-dideoxy-4,7,8,9-tetra-O-acetyl-α-D-glycero-D-galacto-2-nonulopyranosid)onate:

Preparation 1:

In 100 ml of dichloromethane was dissolved 1 g (1.8814 mmole) of methyl(2-propenyl 5-acetamido-4,7,8,9-tetra-O-acetyl-α-D-glycero-D-galacto-2-nonulopyranosid)onate, and after ozonide oxygen was introduced therein for 2.5 hours under cooling at $-78°$ C., nitrogen was passed through the reaction mixture by returning to room temperature to remove excess ozone. Next, 60 ml of acetic acid and 1.2 g of zinc powder were added thereto and the mixture was stirred at room temperature for 43 hours. The reaction suspension was carried out with suction filtration, and the resulting filtrate was evaporated under reduced pressure to obtain 2.28 g of residue. The residue was dissolved in a small amount of chloroform, and applied to a silica gel column chromatography column (Wako gel C-300, 230 g). It was developed by 50 ml of chloroform and a mixed solution of chloroform: ethanol=20:1 and collected by fractions. The solvent was distilled off from the fractions containing the desired compound which was obtained by TLC analysis to give 900 mg (yield=90%) of white powder.

Preparation 2:

In 300 ml of methanol was dissolved 3 g (5.6442 mmole) of methyl(2-propenyl 5-acetamido-4,7,8,9-tetra-O-acetyl-3,5-dideoxy-α-D-glycero-D-galacto-2-nonulopyranosid)onate, and after ozonide oxygen was introduced therein for 3 hours under cooling at $-76°$ C., 8 ml of dimethylsulfide was added thereto and the mixture was stirred at room temperature overnight. The reaction mixture was distilled and ethyl acetate was added to the residue. The mixture was washed with water and then saturated saline solution, dried over anhydrous sodium sulfate and then the solvent was distilled off (crude yield=2.903 g).

This product showed silica gel TLC: RF=0.48 (chloroform : methanol=10:1) and the measured value of $^1$H-NMR (500 MHz, CDCl$_3$, TMS) agreed with the substance obtained by the above Preparation 1.

Physical properties of the product:

Elemental analysis $C_{22}H_{31}NO_{14}.17/20H_2O = 548.80$ (MW=533.49)
Calculated C: 48.15, H: 6.01, N: 2.55,
Found C: 48.16, H: 5.82, N: 2.49, Structural formula

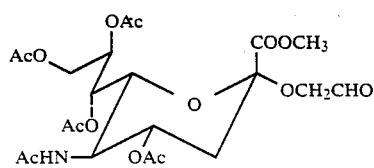

$[\alpha]_D^{23.7}$ −11.23° (C = 0.5, methanol)

IR $\nu_{max}^{KBr}$ cm$^{-1}$: 3400 (—NH—),
1740 (—COOCH$_3$, —CHO),
1660 (—CONH),
1540 (—CONH, amide II)

-continued $^1$H-NMR$^{ppm}_{400\,MHz}$ (CDCl$_3$, TMS)

1.895 (3H, s, —NHCOCH$_3$),
2.048;2.144;2.148 (12H, all s, —OCOCH$_3$ × 4),
2.699 (1H, dd, J$_{3ax,3eq}$ = 12.8Hz, J$_{3eq,4}$ = 4.9Hz, H$_{3eq}$),
3.814 (3H, s, —COOCH$_3$),
4.038 to 4.089 (3H, m, H-5, H-6, H-9′),
4.167 (1H, dd, J = 18.0Hz, J = 0.6Hz, —CH—CHO),
  |
  H
4.248 (1H, dd, J$_{9,9'}$ = 12.5Hz, J$_{8,9}$ = 2.4Hz, H-9),
4.372 (1H, dd, J = 18.0Hz, J = 0.6Hz, —CH—CHO),
  |
  H
4.949 (1H, ddd, J$_{3ax,4}$ = 12.2Hz, J$_{4,5}$ = 9.8Hz, J$_{3eq,4}$ = 4.9Hz, H-4),
5.155 to 5.132 (1H, m, —NHCOCH$_3$),
5.307 (1H, dd, J$_{7,8}$ = 8.9Hz, J$_{6,7}$ = 1.5Hz, H-7),
5.351 (1H, ddd, J$_{7,8}$ = 8.9Hz, J$_{8,9'}$ = 5.5Hz, J$_{8,9}$ = 2.4Hz, H-8),
9.630 (1H, t, J = 0.6Hz, —CHO)

EXAMPLE 2

Synthesis of methyl(carboxymethyl 5-N-acetyl-3,5-dideoxy-4,7,8,9-tetra-O-acetyl-α-D-glycero-D-galacto-2-nonulopyranosid)onate:

Preparation 1:

After 60 mg (0.38 mmole) of potassium permanganate and 141 mg (0.38 mmole) of dicyclohexyl-18-crown-6 in 2 ml of anhydrous benzene solution were stirred for 30 minutes, 100 mg (0.19 mmole) of methyl(2-propenyl-5-acetamido-4,7,8,9-tetra-O-acetyl-3,5-dideoxy-α-D-glycero-D-galacto-2-nonulopyranosid)onate was added thereto and the mixture was stirred at room temperature for 24 hours. To the reaction mixture was added 5 ml of a saturated sodium hydrogen carbonate aqueous solution to make it alkaline, and then the mixture was filtered and the filtrate was washed with water. An aqueous layer separated from a benzene layer was further washed with benzene, the resulting aqueous layer was adjusted to pH 2 with diluted hydrochloric acid, extracted with ethyl acetate and dried over magnesium sulfate. The drier was filtered off and the filtrate was distilled to remove the solvent under reduced pressure to give 120 mg of the residue.

The residue was dissolved in a small amount of chloroform and applied to silica gel chromatography column (Wako gel C-30, 12 g). It was developed by a mixed solution of chloroform: ethanol=8:1 and collected by fractions.

The solvent was distilled off from the fractions containing the desired compound which was obtained by TLC analysis, and the residue was dried under vacuum to give 52 mg (yield=50.5%) of white powder.

Preparation 2:

After 158 mg (1 mmole) of potassium permangenete and 372.5 mg (1 mmole) of dicyclohexyl-18-crown-6 in 5 ml of anhydrous benzene solution were stirred at room temperature for an hour, 267 mg (0.5 mmole) of methyl(formylmethyl 5-N-acetyl-3,5-dideoxy-4,7,8,9-tetra-O-acetyl-α-D-glycero-D-galacto-2-nonulopyranosid)onate was added thereto and the mixture was stirred at room temperature for 24 hours. To the reaction mixture was added an aqueous saturated sodium hydrogen carbonate solution to make it alkaline, and then the mixture was filtered and the filtrate was washed with water. An aqueous layer separated from a benzene layer was further washed with benzene. The resulting aqueous layer was adjusted to pH 3 with diluted hydrochloric acid, extracted with ethyl acetate and dried over magnesium sulfate. The drier was removed by filtration, and the filtrate was distilled from the solvent under reduced pressure to give 320 mg of residue.

The residue was dissolved in a small amount of chloroform and applied to silica gel chromatography column (Wako gel C-30, 0.32 g). It was developed by a mixed solution of chloroform: ethanol=10:1 and collected by fractions.

The solvent was distilled off from the fractions containing the desired compound which was obtained by TLC analysis, and the residue was dried under vacuum to give 210 mg (yield=56.4%) of white powder.

This product completely agreed with those obtained by the above Preparation 1 by the results of instrumental analysis.

Preparation 3:

In 5 ml of acetonitrile was dissolved 2.6 g (5.6442 mmole) of a product obtained in Example 1, an aqueous solution of 2 ml of water dissolved therein 160 mg of monosodium phoshate dihydrate and after 0.5 ml of a 35% hydrogen peroxide aqueous solution was added thereto under cooling at 5° C., 800 mg of sodium chlorite dissolved in 7 ml of water was added thereto little by little (pH=4 to 3). After 3 hours, a small amount of sodium sulfite was added to the reaction mixture and the mixture was stirred at room temperature overnight. After the reaction mixture was adjusted to pH 3 to 2 by a diluted hydrochloric acid, it was extracted with chloroform, washed with water and then with a saturated saline solution, dried over anhydrous magnesium sulfate, and then the solvent was distilled off (yield=2.572 g).

The silica gel TLC: Rf=0.15 (chloroform: methanol=10:1) and measured values by $^1$H-NMR (500 MHz, CDCl$_3$, TMS) of this product agreed with those obtained by the above Preparation 1.

Physical properties of the product:

Elemental analysis C$_{22}$H$_{31}$No$_{15}$.1/5H$_2$O=553.09 (MW=549.48)
Calculated C: 47.78, H: 5.72, N: 2.53,
Found C: 47.74, H: 5.91, N: 2.05, Structural formula

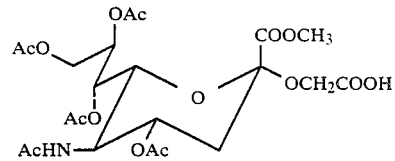

IR $\nu^{KBr}_{max}$ cm$^{-1}$: 3400 (—NH—),
  1740 (—COOCH$_3$, —COOH),
  1640 (—CONH),
  1550 (—CONH, amide II)

$^1$H-NMR$^{ppm}_{400\,MHz}$ (CDCl$_3$, TMS)

1.900 (3H, s, CH$_3$CONH—),
2.033 (1H, dd, J$_{3ax,3eq}$ = 13.1Hz, J$_{3ax,4}$ = 11.6Hz, H$_{3ax}$),
2.045;2.049;2.145 (12H, all s, —OCOCH$_3$ × 4),
2.714 (1H, dd, J$_{3ax,3eq}$ = 13.1Hz, J$_{3eq,4}$ = 4.7Hz, H$_{3eq}$),
3.816 (3H, s, —COOCH$_3$),
4.00 to 4.06 (2H, m, H-6, H-5), -continued 4.082 (1H, dd, $J_{9,9'}$ = 12.1Hz, $J_{8,9'}$ = 5.9Hz, H-9'),
4.291 (1H, dd, $J_{9,9'}$ = 12.1Hz, $J_{8,9}$ = 2.6Hz, H-9),
4.258 (1H, d, J = 16.6Hz, —O—C$\underline{H}$—COOH),
4.366 (1H, d, J = 16.6Hz, —O—C$\underline{H}$—COOH),
4.975 (1H, ddd, $J_{3ax,4}$ = 11.6Hz, $J_{4,5}$ = 10.1Hz, $J_{3eq,4}$ = 4.7Hz, H-4),
5.302 (1H, dd, $J_{7,8}$ = 8.6Hz, $J_{6,7}$ = 1.4Hz, H-7),
5.347 to 5.376 (1H, m, —N$\underline{H}$COCH$_3$),
5.385 (1H, ddd, $J_{7,8}$ = 8.6Hz, $J_{8,9'}$ = 5.9Hz, $J_{8,9}$ = 2.6Hz, H-8),

EXAMPLE 3

Synthesis of methyl(carboxymethyl 5-N-acetyl-3,5-dideoxy-α-D-glycero-D-galacto-2-nonulopyranosid)onate To 10 ml of an anhydrous methanol solution dissolved therein 633 mg (1.152 mmole) of methyl(carboxymethyl 5-N-acetyl-3,5-dideoxy-4,7,8,9-tetra-O-acetyl-α-D-glycero-D-galacto-2-nonulopyranosid)onate was added, under ice-cooling, a solution prepared by dissolving 27 mg (1.152 mmole) of metallic sodium in 10 ml of anhydrous methanol and the mixture was stirred for 3 hours. Thereafter, the mixture was neutralized by Dowex 50W-X8 (H$^+$ type) and then the resin was filtered off, the residue was condensed to dryness to give 417 mg (yield=95%) of amorphous solid.

Physical properties of the product:

Structural formula

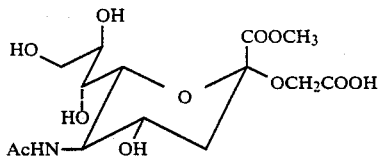

IR $\nu_{max}^{KBr}$ cm$^{-1}$: 3400 (—OH),
1740 (—COOCH$_3$, —COOH),
1640 (—CONH),
1550 (—CONH—)

$^1$H-NMR$_{400 MHz}^{ppm}$ (DMSO-d$_6$, TMS)
1.847 (3H, s, —NHCOC$\underline{H}_3$),
3.684 (3H, s, —COOC$\underline{H}_3$),
4.162 (1H, d, J = 16.5Hz, —O—C$\underline{H}$—COOH),
4.218 (1H, d, J = 16.5Hz, —O—C$\underline{H}$—COOH),

EXAMPLE 4

Synthesis of methyl(9-octadecenyl 5-N-acetyl-3,5-dideoxy-4,7,8,9-tetra-O-acetyl-α-D-glycero-D-galacto-2-nonulopyranosid)onate A suspension comprising 1 g (1.9611 mmole) of methyl 2-chloro-4,7,8,9-tetra-O-acetyl-β-D-N-acetyl-neuraminate, 421 mg (1.5689 mmole) of oleyl alcohol and 1 g of molecular sieves 4A suspended in 20 ml of tetrahydrofuran was stirred under argon atmosphere at room temperature for 30 minutes. Then, 620 mg (2.5306 mmole) of silver salicylate was added thereto and the mixture was further stirred for 20 hours. The reaction suspension was filtered through celite and washed with ethyl acetate. The filtrate and washing solution were combined and the solvent was distilled under reduced pressure to give 1.75 g of residue.

The residue was dissolved in chloroform and applied to a silica gel chromatography column (Wako gel C-300, 200 g). It was developed by a mixed solution of ether:chloroform:toluene:methanol=10:5:5:1) and collected by fractions. The solvent was distilled off from the fractions containing the desired compound which was obtained by TLC analysis, and the residue was dried under vacuum to give 1.22 g (yield=83.6%) of white powder.

Physical properties of the product:

Elemental analysis C$_{38}$H$_{63}$NO$_{13}$.4/5H$_2$O=756.33 (MW=741.91)
Calculated C:60.35, H:8.61, N:1.85,
Found C:60.28, H:8.20, N:2.03, Structural formula

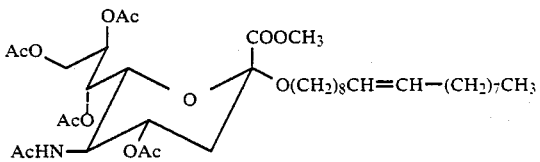

IR $\nu_{max}^{KBr}$ cm$^{-1}$: 3420 (—NH—),
1750 (—COOCH$_3$),
1650 (—CONH—), $^1$H-NMR$_{400 MHz}^{ppm}$ (CDCl$_3$, TMS)
0.882 (3H, t, J = 6.8Hz. —CH$_3$).
1.885 (3H, s, C$\underline{H}_3$CONH—),
2.028;2.043;2.138;2.148 (12H, all s, —OCOCH$_3$ × 4),
2.583 (1H, dd, $J_{3ax,3eq}$ = 12.9Hz, $J_{3eq,4}$ = 4.5Hz, H$_{3eq}$),
3.201 (1H, dt, J = 9.1Hz, J = 6.4Hz, —OC$\underline{H}$—CH$_2$—),
3.750 (1H, dt, J = 9.1Hz, J = 6.4Hz, —OC$\underline{H}$—CH$_2$—),
3.792 (3H, s, —COOCH$_3$),
4.027 to 4.098 (2H, m, H-5, H-6),
4.112 (1H, dd, $J_{9,9'}$ = 12.5Hz, $J_{8,9'}$ = 5.6Hz, H-9'),
4.312 (1H, dd, $J_{9,9'}$ = 12.5Hz, $J_{8,9}$ = 2.6Hz, H-9),
4.842 (1H, ddd, $J_{3ax,4}$ = 12.9Hz, $J_{4,5}$ = 9.7Hz, $J_{3eq,4}$ = 4.5Hz, H-4),
5.148 (1H, m, $J_{NH,H}$ = 9.3Hz, —N$\underline{H}$COCH$_3$),
5.300 to 5.370 (3H, m, H-7, CH$_2$C$\underline{H}$=C$\underline{H}$CH$_2$—),
5.397 (1H, ddd, $J_{7,8}$ = 8.2Hz, $J_{8,9'}$ = 5.6Hz, $J_{8,9}$ = 2.6Hz, H-8),

EXAMPLE 5

Synthesis of methyl(8-formyloctyl 5-N-acetyl-3,5-dideoxy-4,7,8,9-tetra-O-acetyl-α-D-glycero-D-galacto-2-nonulopyranosid)onate:

In 100 ml of methylene chloride was dissolved 2.14 g (2.8844 mmole) of methyl(9-octadecenyl 5-N-acetyl-3,5-dideoxy-4,7,8,9-tetra-O-acetyl-3,5-dideoxy-α-D-glycero-D-galacto-2-nonulopyranosid)onate, and after ozonide oxygen was introduced therein for 3 hours under cooling at −78° C., nitrogen passed through the reaction mixture by returning to room temperature to remove excess ozone. Next, 100 ml of acetic acid, and 2 g of zinc powder were added thereto and the mixture was stirred at room temperature for 42 hours. The reaction suspension was carried out by suction filtration, and the resulting filtrate was evaporated under reduced pressure to obtain 2.71 g of residue. The residue was developed by a small amount of a mixed solution of chloroform:ethyl acetate:toluene:ethanol=10:5:5:2 and collected by fractions.

The solvent was distilled off from the fractions containing the desired compound which was obtained by TLC analysis to give 1.49 g (yield=81.9%) of white powder.

Physical properties of the product:

Elemental analysis $C_{29}H_{45}NO_{14}.9/10H_2O=647.89$ (MW=631.67)
Calculated C:53.76, H:7.28, N:2.16,
Found C:53.71, H:7.13, N:2.49, Structural formula

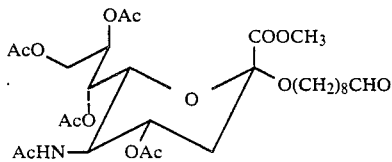

IR $\nu_{max}^{KBr}$ cm$^{-1}$: 3450 (—NH—),
  2930 (—CH$_2$—),
  1740 (—COOCH$_3$, —CHO),
  1660 (—CONH—),
  1550 (—CONH, amide II), $^1$H-NMR$_{400\ MHz}^{ppm}$ (CDCl$_3$, TMS)

1.884 (3H, s, C$\underline{H}_3$CONH—),
  1.949 (1H, t, J = 12.8Hz, H$_{3ax}$),
  2.025;2.045;2.136;2.148 (12H, all s, —OCOCH$_3$ × 4),
  2.343 (2H, t, J = 7.3Hz, —CH$_2$C$\underline{H}_2$CHO),
  2.577 (1H, dd, J$_{3ax.3eq}$ = 12.8Hz, J$_{3eq.4}$ = 4.6Hz, H$_{3eq}$),
  3.219 (1H, dt, J = 9.3Hz, J = 6.5Hz, —O—C$\underline{H}$—CH$_2$—),
  3.747 (1H, dt, J = 9.3Hz, J = 6.5Hz, —O—C$\underline{H}$—CH$_2$—),
  3.792 (3H, s, —COOCH$_3$),
  4.28 to 4.14 (2H, m, H-5, H-6),
  4.111 (1H, dd, J$_{9.9'}$ = 12.4Hz, J$_{8.9'}$ = 5.5Hz, H-9'),
  4.313 (1H, dd, J$_{9.9'}$ = 12.4Hz, J$_{8.9}$ = 2.6Hz, H-9),
  4.839 (1H, ddd, J$_{3ax.4}$ = 12.4Hz, J$_{4.5}$ = 9.9Hz, J$_{3eq.4}$ = 4.6Hz, H-4),
  5.169 (1H, d, J = 9.6Hz, —CONH—),
  5.329 (1H, dd, J$_{7.8}$ = 8.3Hz, J$_{6.7}$ = 1.7Hz, H-7),
  5.391 (1H, ddd, J$_{7.8}$ = 8.3Hz, J$_{8.9'}$ = 5.5Hz, J$_{8.9}$ = 2.6Hz, H-8),

EXAMPLE 6

Synthesis of methyl(8-carboxyoctyl 5-N-acetyl-3,5-dideoxy-4,7,8,9-tetra-O-acetyl-α-D-glycero-D-galacto-2-nonulopyranosid)onate:

After 110 mg (0.699 mmole) of potassium permanganate and 196 mg (0.5256 mmole) of dicyclohexyl-18-crown-6 in 5 ml of anhydrous benzene solution were stirred at room temperature for an hour, 166 mg (0.2628 mmole) of methyl(8-formyloctyl 5-N-acetyl-3,5-dideoxy-4,7,8,9-tetra-O-acetyl-3,5-dideoxy-α-D-glycero-D-galacto-2-nonulopyranosid)-onate was added thereto and the mixture was stirred at room temperature for 20 hours. To the reaction mixture was added 30 ml of a saturated sodium hydrogen carbonate aqueous solution to make it alkaline, and then the mixture was filtered and the filtrate was washed with water. An aqueous layer separated from a benzene layer was further washed with benzene, the resulting aqueous layer was adjusted to pH 3 with diluted hydrochloric acid, extracted with ethyl acetate and dried over magnesium sulfate. After the drier was filtered off, the filtrate was distilled to remove the solvent under reduced pressure to give 205 mg of residue.

The residue was dissolved in chloroform and applied to a silica gel chromatography column (Wako gel C-30, 21 g). It was developed by a mixed solution of chloroform:ethylacetate:toluen:ethanol=10:5:5:2 and collected by fractions.

The solvent was distilled off from the fractions containing the desired compound which was obtained by TLC analysis, and the residue was dried under vacuum to give 128 mg (yield =75.3%) of white powder..

Physical properties of the product:

Elemental analysis $C_{29}H_{45}NO_{15}=647.67$
Calculated C:53.78, H:7.00, N:2.16,
Found C:53.67, H:7.06, N:2.03, Structural formula

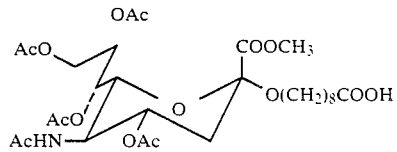

IR $\nu_{max}^{KBr}$ cm$^{-1}$: 3400 (—NH—, —COO$\underline{H}$),
  1750 (—COOCH$_3$, —COOH),
  1660 (—CONH—),
  1550 (—CONH, amide II)

$^1$H-NMR$_{400\ MHz}^{ppm}$ (CDCl$_3$, TMS)

1.883 (3H, s, —NHCOCH$_3$),
  2.025, 2.043, 2.134, 2.146 (12H, all s, —OCOCH$_3$ × 4),
  1.953 (1H, t, J=12.6 Hz, H$_{3ax}$),
  2.340 (2H, t, J=7.4 Hz, —C$\underline{H}_2$COOH),
  2.574 (1H, dd, J$_{3ax.3eq}$=12.8 Hz, J$_{3eq.4}$=4.7 Hz, H$_{3eq}$),
  3.211 (1H, dt, J=9.3 Hz, J=6.4 Hz, —OC$\underline{H}$—CH$_2$—),
  3.744 (1H, dt, J=9.3 Hz, J=6.4 Hz, —OC$\underline{H}$—CH$_2$—),
  3.789 (3H, s, —COOCH$_3$),
  4.008 to 4.108 (2H, m, H-6, H-5),
  4.109 (1H, dd, J$_{9.9'}$=12.5 Hz, J$_{8.9'}$=5.5 Hz, H-9'),
  4.312 (1H, dd, J$_{9.9'}$=12.5 Hz, J$_{8.9}$=2.6 Hz, H-9),
  4.836 (1H, ddd, J$_{3ax.4}$=12.6 Hz, J$_{4.5}$=9.7 Hz, J$_{3eq.4}$=4.7 Hz, H-4),
  5.234 (1H, d, J$_{NHCH}$=9.3 Hz, —CONH—),
  5.327 (1H, d, J$_{7.8}$=8.2 Hz, J$_{6.7}$=1.7 Hz, H-7),
  5.388 (1H, ddd, J$_{7.8}$=8.2 Hz, J$_{8.9'}$=5.5 Hz, J$_{8.9}$=2.6 Hz, H-8),

EXAMPLE 7

Synthesis of methyl(8-carboxyoctyl 5-N-acetyl-3,5-dideoxy-α-D-glycero-D-galacto-2-nonulopyranosid)onate:

To 100 mg (0.145 mmole) of methyl(8-carboxyoctyl 5-N-acetyl-3,5-dideoxy-4,7,8,9-tetra-O-acetyl-α-D-glycero-D-galacto-2-nonulopyranosid)onate dissolved in 10 ml of anhydrous methanol solution was added 4.6 mg (0.2 mmole) of metallic sodium under ice-cooling and the mixture was stirred at room temperature for 6 hours. Thereafter, the mixture was neutralized by Dowex 50W-X8 (H+ type), and then the resin was filtered off, the filtrate was condensed to dryness to give 70 mg (yield=95%) of residue.

Physical properties of the product:

Structural formula

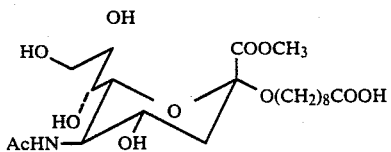

IR $\nu_{max}^{KBr}$ cm$^{-1}$: 3400 (—OH),
1740 (—COOCH$_3$, —COOH),
1650 (—CONH),
1570 (—CONH, amide II)

$^1$H-NMR$_{500\ MHz}^{ppm}$ (CD$_3$OD, TMS)

1.989 (3H, s, —NHCOC$\underline{H}_3$), 2.262 (2H, t, J=7.7 Hz, —C$\underline{H}_2$COOH), 2.668 (1H, dd, J=4.4 Hz, 12.8 Hz, H$_{3eq}$), 3.830 (3H, s, —COOC$\underline{H}_3$),

EXAMPLE 8

Synthesis of N-[(methyl 5-acetamido-4,7,8,9-tetra-O-acetyl-3,5-dideoxy-α-D-glycero-D-galacto-2-nonulopyranosylonate)oxyacetyl]-L-alanine methyl ester:

Preparation 1:

To 8 ml of dimethylformamide solution dissolved therein 256 mg (0.4659 mmole) of methyl(carboxymethyl 5-N-acetyl-3,5-dideoxy-4,7,8,9-tetra-O-acetyl-α-D-glycero-D-galacto-2-nonulopyranosid)onate, 65 mg (0.4659 mmole) of L-alanine methyl ester hydrochloride, 107 mg (0.5691 mmole) of WSC (1-ethyl-3-(3-dimethylaminopropyl)carbodiimide hydrochloride) and 83 mg (0.4659 mmole) of HONB (N-hydroxy-5-norbornene-2,3-dicarboximide) was added 47 mg (0.4659 mmole) of N-methylmorpholine and the mixture was stirred under ice-cooling for an hour and then at room temperature for 24 hours.

The reaction mixture was sucked off and the resulting filtrate was distilled to remove the solvent under reduced pressure to give 690 mg of oily product.

This oily product was dissolved in a small amount of methanol, applied to Sephadex LH-20 chromatography column (2×40 cm) and developed by methanol to collect fractions.

The solvent was distilled off from the fractions containing the desired compound which was obtained by TLC analysis, and the residue was dried under vacuum to give 215 mg (yield=72.6%) of white powder.

Preparation 2:

In 3 ml of dimethylformamide were dissolved 36 mg (56 μmole) of the product obtained in Example 16 mentioned below and 13 mg (73 μmole) of L-alanine methyl ester hydrochloride, 0.5 ml of N-methylmorpholine was added thereto and the mixture was stirred at room temperature overnight. The reaction mixture was distilled to remove the solvent and the residue was extracted with ethyl acetate, washed with water and then with a saturated saline solution, dried over anhydrous magnesium sulfate and then the solvent was removed. The residue obtained was purified through Sephadex HL-20 chromatography column (eluted by methanol) (yield=18.5 mg, yield=51.7%).

This product showed silica gel TLC: Rf=0.96 (chloroform:methanol=10:1) and the measured values of $^1$H-NMR (500 MHz, CDCl$_3$, TMS) agreed with those of the substance obtained by the above Preparation 1.

Preparation 3:

In pyridine 1 ml./acetic anhydride 1 ml was dissolved 82.0 mg (0.176 mmole) of the product obtained in Example 12 mentioned below, and the mixture was stirred at room temperature overnight. The reaction mixture was distilled and the residue was purified through silica gel column chromatography (C-300, 20 g, chloroform:methanol=5:1) (yield=62 mg, yield=56%).

The silica gel TLC:Rf=0.96 (chloroform:methanol=10:1) and the measured values of $^1$H-NMR (500 MHz, CDCl$_3$, TMS) agreed with those of the substance obtained by the above Preparation 1.

Physical properties of the product:

Elemental analysis C$_{26}$H$_{38}$N$_2$O$_{16}$·1/5H$_2$O=638.19 (MW=634.59)
Calculated C:48.93, H:6.06, N:4.39,
Found C:48.88, H:5.99, N:4.21, Structural formula

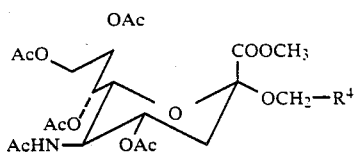

wherein —R$^4$ represents —CONH—CH—COOCH$_3$
                                        |
                                       CH$_3$ IR $\nu_{max}^{KBr}$ cm$^{-1}$: 3400 (—NH—),
1750 (—COOCH$_3$),
1670 (—CONH—),
1540 (—CONH, amide II), $^1$H-NMR$_{400\ MHz}^{ppm}$ (CDCl$_3$, TMS)

1.441 (3H, d, J=7.2 Hz, —C$\underline{H}$—),
$\qquad\qquad\qquad\qquad\ \ $ |
$\qquad\qquad\qquad\ \ $ CH$_3$ 1.898 (3H, s, —NHCOCH$_3$),
2.039, 2.042, 2.120, 2.128 (12H, all s, —OCOCH$_3$ × 4),
2.050 (1H, dd, J$_{3ax,3eq}$=13.0 Hz, J$_{3eq,4}$=11.5 Hz, H$_{3ax}$),
2.673 (1H, dd, J$_{3ax,3eq}$=13.0 Hz, J$_{3eq,4}$=4.8 Hz, H$_{3eq}$),
3.765 (3H, s, COOCH$_3$, alanine),
3.822 (3H, s, 2-COOCH$_3$)

4.001 (1H, d, J=15.2 Hz, —OC$\underline{H}$CO—),
$\qquad\qquad\qquad\qquad\qquad\ \ $ |
$\qquad\qquad\qquad\qquad\qquad\ \ $ H 4.012 to 4.086 (1H, m, H-5),
4.095 (1H, dd, J$_{9,9'}$=12.5 Hz, J$_{8,9'}$=5.7 Hz, H-9'),
4.187 (1H, dd, J$_{5,6}$=10.8 Hz, J$_{6,7}$=2.0 Hz, H-6),
4.268 (1H, dd, J$_{9,9'}$=12.5 Hz, J$_{8,9}$=2.6 Hz, H-9), 4.286 (1H, d, J=15.2 Hz, —OC$\underline{H}$—CO—).
$\qquad\qquad\qquad\qquad\qquad\ \ $ |
$\qquad\qquad\qquad\qquad\qquad\ \ $ H -continued
Structural formula 4.633 (1H, q, J=7.3 Hz, —CONHC$\underline{H}$—),
         |
         CH$_3$ 5.007 (1H, ddd, J$_{3ax,4}$=11.5 Hz, J$_{4,5}$=10.5 Hz, J$_{3eq,4}$=4.8 Hz, H-4),
5.243 (1H, d, J=5.2 Hz, —CONH—),
5.300 (1H, dd, J$_{8,7}$=8.2 Hz, J$_{6,7}$=2.0 Hz, H-7),
5.372 (1H, ddd, J$_{8,7}$=8.2 Hz, J$_{8,9'}$=5.7 Hz, J$_{8,9}$=2.6 Hz, H-8),
5.305 (1H, d, J=6.1 Hz, —CONH—)

EXAMPLE 9

Synthesis of Nα-CBZ-Nε-[(methyl 5-acetamido-4,7,8,9-tetra-O-acetyl-3,5-dideoxy-α-D-glycero-D-galacto-2-nonulopyranosylonate)oxyacetyl]-L-lysine methyl ester To 10 ml of a dimethylformamide solution dissolved therein 275 mg(0.5 mmole) of methyl(carboxymethyl 5-N-acetyl-3,5-dideoxy-4,7,8,9-tetra-O-acetyl-α-D-glycero-D-galacto-2-nonulopyranosid)onate, 165.4 mg (0.5 mmole) of N-α-CBZ-L-lysine methyl ester HCl salt (CBZ represents benzyloxycarbonyl group, hereinafter the same meaning), 115 mg (0.6 mmole) of WSC [1-ethyl-3-(3-dimethylaminopropyl)-carbodiimide HCl salt] and 89.6 mg (0.5 mmole) of HONB (N-hydroxy-5-norbornen-2,3-dicarboximide) was added 50.6 mg (0.5 mmole) of N-methylmorpholine and the mixture was sucked and the resulting filtrate was distilled to remove the solvent to give 1.2167 g of oily product. This oily product was dissolved in a small amount of methanol, applied to Sephadex LH-20 chromatography column (2×40 cm) and developed with methanol and collected by fractions. The solvent was distilled off from the fractions containing the desired compound which was obtained by TLC analysis to give 341 mg (yield=82.6%) of white powder.

Physical properties of the product:

Elemental analysis C$_{37}$H$_{51}$N$_3$O$_{18}$=825.82
Calculated C:53.81, H:6.22, N:5.09,
Found C:53.81, H:6.12, N5.06, Structural formula

[Structure diagram: OAc, AcO, AcO, AcHN, OAc, O, COOCH$_3$, OCH$_2$—R$^5$]

wherein —R$^5$ represents —CONH—(CH$_2$)$_4$—C$\underline{H}$—COOCH$_3$
                                                           |
                                                           NH—CBz IR ν$_{max}^{KBr}$ cm$^{-1}$: 3400 (—NH—),
              1750 (—COOCH$_3$, —NHOCOCH$_2$—),
              1670 (—CONH—),
              1540 (—CONH, amide II), $^1$H-NMR$_{400 MHz}^{ppm}$ (CDCl$_3$, TMS)

1.890 (3H, s, —NHCOC$\underline{H}_3$),
2.014 (1H, dd, J$_{3ax,3eq}$=12.9 Hz, J$_{3ax,4}$=11.7 Hz, H$_{3ax}$),
2.032; 2.035; 2.115; 2.127 (12H, all s, —OCOC$\underline{H}_3$ × 4),
2.630 (1H, dd, J$_{3ax,3eq}$=12.9 Hz, J$_{3eq,4}$=4.8 Hz, H$_{3eq}$),
3.743 (3H, s, —COOC$\underline{H}_3$, lysine),
3.803 (3H, s, 2-COOC$\underline{H}_3$).

-continued
Structural formula

H
                |
3.988 (1H, d, J=15 Hz, —O—C$\underline{H}$—CONH—), 4.067 (1H, dd, J$_{9,9'}$=12.3 Hz, J$_{8,9'}$=5.7 Hz, H-9'),
4.138 (1H, dd, J$_{5,6}$=10.8 Hz, J$_{6,7}$=1.8 Hz, H-6), H
                |
4.202 (1H, d, J=15 Hz, —O—C$\underline{H}$—CONH—), 4.272 (1H, dd, J$_{9,9'}$=12.3 Hz, J$_{8,9}$=2.5 Hz, H-9), NH
                |
4.363 (1H, m, CH$_3$OOC—C$\underline{H}$—), 4.956 (1H, ddd, J$_{3ax,4}$=11.7 Hz, J$_{4,5}$=9.8 Hz, J$_{3eq,4}$=4.8 Hz, H-4),
5.108 (2H, s, —COOC$\underline{H}_2$-φ),
5.297 (1H, dd, J$_{7,8}$=8.3 Hz, J$_{6,7}$=1.8 Hz, H-7),
5.325 (1H, ddd, J$_{8,9}$=2.5 Hz, J$_{8,9'}$=5.7 Hz, J$_{7,8}$=8.3 Hz, H-8),
7.31 to 7.36 (5H, m, phenyl-H)

EXAMPLE 10

Synthesis of N-(9-[(methyl 5-acetamido-4,7,8,9-tetra-O-acetyl-3,5-dideoxy-α-D-glycero-D-galacto-2-nonulopyranosylonate)oxy]nonanoyl-L-alanine methyl ester:

To 10 ml of a dimethylformamide solution dissolved therein 250 mg (0.44 mmole) of methyl(8-carboxyoctyl 5-N-acetyl-3,5-dideoxy-4,7,8,9-tetra-O-acetyl-α-D-glycero-D-galacto-2-nonulopyranosid)onate, 65 mg(0.466 mmole) of L-alanine methyl ester HCl salt, 107 mg (0.466 mmole) of WSC and 83 mg (0.466 mmole) of HONB was added 47 mg (0.466 mmole) of N-methylmorpholine and the mixture was stirred at room temperature for a whole day and night. After ethyl acetate was added to the reaction mixture to extract, the extract was washed with water and then with a saturated saline solution. It was dried over anhydrous magnesium sulfate, and distilled to remove the solvent, the obtained residue was purified through silica gel chromatography column (Wako gel C-300, 50 g, ethyl acetate) to give 249 mg (yield=86.8%) of oily product.

Physical properties of the product:

Structural formula

[Structure diagram: OAc, AcO, AcO, AcHN, OAc, O, COOCH$_3$, O(CH$_2$)$_8$—R$^4$]

CH$_3$
                                                           |
wherein —R$^4$ represents —CONH—CH—COOCH$_3$ IR ν$_{max}^{KBr}$ cm$^{-1}$: 3300 (—NH—),
              1750 (—COOCH$_3$),
              1660 (—CONH—),
              1540 (—CONH, amide II).

$^1$H-NMR$_{400 MHz}^{ppm}$ (CDCl$_3$, TMS)

-continued
Structural formula 1.400 (3H, d, J=7.0 Hz, —CH—C$\underline{H}_3$), 1.882, 2.026, 2.043, 2.137, 2.146 (15H, all s, —OCOCH$_3$ × 5),
1.95 (1H, t, J=12.8 Hz, H$_{3ax}$),
2.58 (1H, dd, J=4.8, 12.8 Hz, H$_{3eq}$),
3.75 (3H, s, —COOCH$_3$, alanine),
3.79 (3H, s, 2-COOCH$_3$), 4.61 (1H, m, —C$\underline{H}$—CH$_3$), 4.84 (1H, ddd, J=4.8, 10.0, 12.8 Hz, H-4)

EXAMPLE 11

Synthesis of Nα-CBZ-Nε-(9-[(methyl 5-acetamido-4,7,-8,9-tetra-O-acetyl-3,5-dideoxy-α-D-glycero-D-galacto-2-nonulopyranosylonate)oxy]-nonanoyl)-L-lysine methyl ester:

To 2 ml of a dimethylformamide solution dissolved therein 67 mg (0.1034 mmole) of methyl(8-carboxyoctyl 5-N-acetyl α-D-glycero-D-galacto-2-nonulopyranosid)onate, 34 mg (0.1034 mmole) of N-α-CBZ-L-lysine methyl ester hydrochloride, 24 mg (0.1241 mmole) of WSC and 19 mg (0.1034 mmole) of HONB was added 10.5 mg (0.1034 mmole) of N-methylmorpholine and the mixture was stirred at room temperature for 20 hours. The reaction mixture was sucked and the resulting filtrate was distilled to remove the solvent under reduced pressure to obtain 170 mg of oily product.

This oily product was dissolved in a small amount of methanol, applied to Sephadex LH-20 chromatography column (2×40 cm) and developed with methanol and collected by fractions.

The solvent was distilled off from the fractions containing the desired compound which was obtained by TLC analysis to give 61 mg (yield=67%) of white powder.

Physical properties of the product:

Structural formula

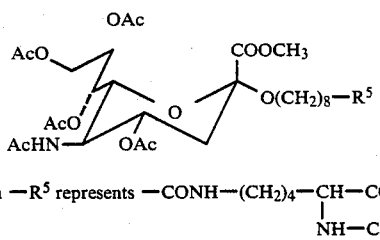

wherein —R$^5$ represents —CONH—(CH$_2$)$_4$—CH—COOCH$_3$
$\phantom{wherein —R^5 represents —CONH—(CH_2)_4—}$ |
$\phantom{wherein —R^5 represents —CONH—(CH_2)_4—}$ NH—CBz $^1$H-NMR$^{ppm}_{400\ MHz}$ (CDCl$_3$, TMS)

1.871 (3H, s, —NHCOCH$_3$),
1.939 (1H, dd, J$_{3ax.3eq}$=12.7 Hz, J$_{3ax.4}$=12.3 Hz, H$_{3ax}$),
2.018, 2.035, 2.127, 2.140 (12H, all s, —OCOCH$_3$ ×4),
2.576 (1H, dd, J$_{3ax.3eq}$=12.7 Hz, J$_{3eq.4}$=4.5 Hz, H$_{3eq}$),
3.738 (3H, s, —CQOCH$_3$, lysine),
3.786 (3H, s, 2-COOCH$_3$),
4.311 (1H, dd, J$_{9,9'}$=12.5 Hz, J$_{8,9}$=2.5 Hz, H-9), $\phantom{4.32 to 4.40 (1H. m. CH_3OCO—}$ NH—
$\phantom{4.32 to 4.40 (1H. m. CH_3OCO—}$ |
4.32 to 4.40 (1H, m, CH$_3$OCO—C$\underline{H}$—CH$_2$—), -continued
Structural formula 4.836 (1H, ddd, J$_{3ax.4}$=12.3 Hz, J$_{4,5}$=9.7 Hz, J$_{3eq.4}$=4.5 Hz, H-4),
5.106 (2H, s, φ-CH$_2$OCO—),
5.322 (1H, dd, J$_{7,8}$=8.2 Hz, J$_{6,7}$=1.7 Hz, H-7),
5.385 (1H, ddd, J$_{7,8}$=8.2 Hz, J$_{8,9'}$=5.6 Hz, J$_{8,9}$=2.5 Hz, H-8),
7.31 to 7.36 (5H, m, phenyl-H)

EXAMPLE 12

Synthesis of N-[(methyl 5-acetamido-3,5dideoxy-α-D-glycero-D-galacto-2-nonulopyranosylonate)oxyacetyl]-L-alanine methyl ester:

Preparation 1:

To 10 ml of a dimethylformamide solution dissolved therein 100 mg (262 μmole) of methyl(carboxymethyl 5-N-acetyl-3,5-dideoxy-α-D-glycero-D-galacto-2-nonulopyranoside)onate, 25.4 mg (262 μmole) of L-alanine methyl ester hydrochloride, 41.8 mg (314 μmole) of WSC and 32.4 mg (262 μmole) of HONB was added 18.4 mg (262 μmole) of N-methylmorpholine under water cooling and stirring, and then the mixture was stirred at room temperature for a whole day and night.

After the reaction mixture was distilled, the residue was purified through silica gel columm chromatography (C-300, 20 g, chloroform:methanol=5:1). Then, it was purified again through Dowex 50 W-X8 to give 75 mg (yield=61.4%) of oily product.

Silica gel TLC:Rf=0.55 (butanol:ethanol:water=2:1:1)

Preparation 2:

In 0.5 ml of dimethylsulfoxide was dissolved 50 mg (1.1 mmole) of a product obtained in Preparation 1 of Example 18 mentioned hereinbelow, methyl iodide was added thereto excessively and the mixture was stirred at room temperature for 1.5 hours. The reaction mixture was purified as it were through silica gel column chromatography (C-300, 10 g, chloroform:methanol=2:1) and among Rf=0.27/0.17 due to silica gel TLC (chloroform:methanol=5:1), the desired substance was obtained from the fractions of Rf=0.17. The measured values of $^1$H-NMR (500 MHz, CDCl$_3$, TMS) were accorded with the substance obtained in the above Preparation 1.

Physical properties of the product:

Structural formula

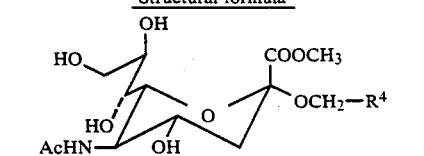

wherein —R$^4$ represents —CONH—CH—COOCH$_3$
$\phantom{wherein —R^4 represents —CONH—}$ |
$\phantom{wherein —R^4 represents —CONH—}$ CH$_3$ IRν$^{KBr}_{max}$ cm$^{-1}$: 3400 (—NH—, —OH),
1740 (—COOCH$_3$),
1660 (—CONH—),
1540 (—CONH, amide II), $^1$H-NMR$^{ppm}_{500\ MHz}$ (CD$_3$OD, TMS)
1.414 (3H, d, J=7.3Hz, —CH$_3$),
1.850 (1H, dd, J=11.3, 12.8Hz, H$_{3ax}$),
2.008 (3H, s, —NHCOCH$_3$), -continued 2.742 (3H, dd, J=4.7, 12.9Hz, H$_{3eq}$),
3.731 (3H, s, —COOCH$_3$, alanine),
3.832 (3H, s, 2-COOCH$_3$), 4.117 (1H, d, J=15.4Hz, —O—CH—CONH—),
                                   |
                                   H 4.286 (1H, d, J=15.4Hz, —O—CH—CONH—),
                                   |
                                   H 4.448 (1H, q, J=7.3Hz, —CH—CH$_3$),
                        |

EXAMPLE 13

Synthesis of N-[(methyl 5-acetamido-4,7,8,9-tetra-O-acetyl-3,5-dideoxy-α-D-glycero-D-galacto-2-nonulopyranosylonate)oxyacetyl]-BSA Preparation 1:

In a 5 ml of solution of water:dioxane=1:1 were dissolved 259 mg (0.4714 mmole) of methyl(carboxymethyl 5-N-acetyl-3,5-dideoxy-4,7,8,9-tetra-O-acetyl-α-D-glycero-D-galacto-2-nonulopyranoside)onate, 108 mg (0.5657 mmole) of WSC and 85 mg (0.4717 mmole) of HONB was added 48 ml of N-methylmorpholine added thereto, and the mixture was stirred at room temperature for an hour. Then, at 6° C. cooling, 10 ml of an aqueous solution dissolved therein 521 mg (7.86 μmole) of BSA (Bovine Serum Albumin) was added thereto and the mixture was stirred for 24 hours. The reaction mixture was sucked and the resulting filtrate was condensed under reduced pressure, and then diluted with 100 ml of water and dialyzed. The residual solution was freeze-dried to obtain 170 mg of colorless amorphous crystals.

Preparation 2:

In 1 ml of dimethylformamide was dissolved 210 mg (327 μmole) of a product obtained in Example 16 mentioned hereinbelow, and the solution was added little by little at 4° C. cooling under stirring to a solution prepared by dissolving 203.8 mg of BSA in 12.9 ml of phosphoric acid buffer (pH=7.5) and the mixture was stirred at 4° C. cooling overnight. The reaction mixture was dialyzed and freeze-dried to obtain the same substance as in the above Preparation 1 (yield=94 mg).

Physical properties of the product:

Structural formula

[Structure: {AcO, AcO, AcHN, OAc} ring with COOCH$_3$ and OCH$_2$CO—BSA]$_m$

IRν$_{max}^{KBr}$ cm$^{-1}$: 1740 (—COOCH$_3$)
$^1$H-NMR$_{500 MHz}^{ppm}$ (D$_2$O, TSP)
1.970 (s, —NHCOCH$_3$),
2.100,2.136,2.208,2.242 (all s, —OCOCH$_3$ × 4),
3.919 (s, —COOCH$_3$).

EXAMPLE 14

Synthesis of [(methyl 5-acetamido-3,5-dideoxy-α-D-glycero-D-galacto-2-nonulopyranosylonate)oxyacetyl]-BSA:

To 20 ml of a solution (DMF:H$_2$O=1:1) of 130 mg (0.3431 mmole) of methyl(carboxymethyl 5-N-acetyl-3,5-dideoxy-α-D-glycero-D-galacto-2-nonulopyranosid)onate, 104 mg (0.543 mmole) of WSC and 81 mg (0.453 mmole) of HONB, was added 10 ml of an aqueous solution dissolved therein 46 mg (0.453 mmole) of N-methylmorpholine and 470 mg (7.093 μmole) of BSA, and the mixture was stirred at room temperature for 24 hours. The reaction mixture was filtered and the resulting filtrate was dialyzed. The residue was freeze-dried to obtain 580 mg of colorless amorphous crystal.

Physical properties of the product:

Structural formula

[Structure: {HO, HO, AcHN, OH} ring with OH, COOCH$_3$ and OCH$_2$CO—BSA]$_m$

EXAMPLE 15

Synthesis of N-[(methyl 5-N-acetyl-4,7,8,9-tetra-O-acetyl-3,5-dideoxy-α-D-glycero-D-galacto-2-nonulopyranosyl onate)oxyacetyl]-D-alanine methyl ester In 5 ml of dimethylformamid were dissolved 200 mg (364 μmole) of the product obtained in Example 2, 50.6 mg (364 μmole) of L-alanine methyl ester hydrochloride, 107 mg (466 μmole) of WSC and 83 mg (466 μmole) of HONB, 47 mg (466 μmole) of N-methylmorpholine was added thereto and the mixture was stirred at room temperature overnight. After distilled the reaction mixture, the residue was purified through silica gel chromatography column (C-300, 30 g, chloroform:methanol=20:1) to obtain 125 mg of a product (yield=54%).

Silica gel TLC: Rf=0.79 (chloroform: methanol=10:1)

Physical properties of the product:

Structural formula

[Structure: AcO, AcO, AcHN, OAc ring with OAc, COOCH$_3$ and OCH$_2$—R$^4$]

wherein —R$^4$ represents —CONH—CH—COOCH$_3$
                                        |
                                        CH$_3$ $^1$H-NMR$_{500 MHz}^{ppm}$ (CDCl$_3$, TMS) δ
1.460 (3H, d, J=7.3Hz, —CH—CH$_3$),
1.895 (3H, s, —NHCOCH$_3$),
2.039;2.041;2.123,2.129 (12H, all s, —OCOCH$_3$ × 4),
2.680 (1H, dd, J=4.8, 12.8Hz, H$_{3eq}$),
3.760 (3H, s, —COOCH$_3$, alanine),
3.825 (3H, s, 2-COOCH$_3$).

3.995 (2H, d, J=15.4Hz, —OCH—CONH—),
         |
         H 4.177 (2H, d, J=15.4Hz), —OCH—CONH—),
         |
         H 4.641 (1H, m, —CH—),
         |
         CH$_3$ 4.946 (1H, m, 4H),
5.378 (1H, m, 8H)

EXAMPLE 16

Synthesis of methyl[(N-succinimidyloxycarbonyl)methyl 5-N-acetyl 3,5-dideoxy-4,7,8,9-tetra-O-acetyl-α-D-glycero-D-galacto-2-nonulopyranosid]onate In 15 ml of acetonitrile were dissolved 101.4 mg (185 μmole) of the product obtained in Example 2 and 232 mg (896 μmole) of N,N'-disuccinimido carbonate (DSC), then 320 ml of anhydrous pyridine was added thereto and the mixture was stirred at room temperature overnight. The reaction mixture was distilled and then added ethyl acetate. The ethyl acetate layer was washed with water and then with a saturated saline solution, dried with anhydrous magnesium sulfate, and the solvent was distilled off to obtain 210 mg of a product.

Silica gel TLC: Rf=0.477 (chloroform:methanol=10:1)

Physical properties of the product:

Structural formula

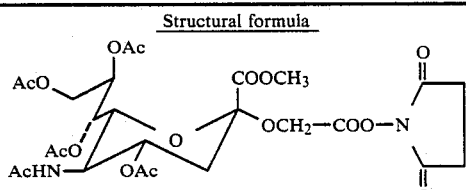

$^1$H-NMR$^{ppm}_{500 MHz}$ (CDCl$_3$, TMS) δ
1.885;2.035;2.049,2.147,2.162
(15H, all s, —OCOCH$_3$ × 5),
2.708 (1H, dd, J=4.6, 13.0Hz, H$_{3eq}$),
2.824 to 2.869 (4H, m, —CO—CH$_2$—CH$_2$—CO—),
3.816 (3H, s, —COCH$_3$),
4.993 (1H, m, 4H), 4.605 (1H, d, J=17.2Hz, —OCHCOO—),
         |
         H 4.708 (1H, d, J=17.2Hz, —OCH—COO—),
         |
         H

EXAMPLE 17

Synthesis of [(sodium 5-N-acetyl-3,5-dideoxy-α-D-glycero-D-galacto-2-nonulopyranosylonate)]oxyacetyl]-BSA:

In 1 ml of water was dissolved 25 mg of the product obtained in Preparation 2 of Example 13, 192 μl of a 0.769N aqueous NaOH solution and the mixture was stirred at room temperature overnight. After the reaction mixture was dialyzed and freeze-dried to obtain 11 mg of a product.

Structural formula

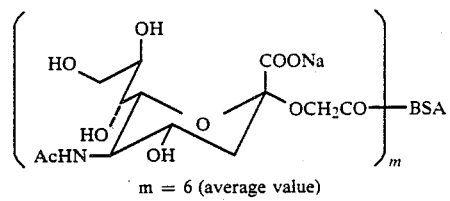

m = 6 (average value)

Determination of the sialic acid by HPLC:

To 5 mg of the above product was added 1 ml of 0.1M H$_2$SO$_4$ and the mixture was stirred under heating at 80° C. for an hour. The reaction mixture was centrifuged and a supernatant was analyzed by injecting 20 μl into HPLC. As a result, binded numbers of the sialic acid residues were 6 in average (m=6) per one molecule of BSA.

HPLC column condition column HPX-87H, 300 mm×7.8 mm (available from Biorad Co.)
Flow rate 0.9 ml/min
Column temperature 42° C.
Eluent 0.1N H$_2$SO$_4$
Detector UV 206 nm

EXAMPLE 18

Synthesis of N-[(sodium 5-N-acetyl-3,5-dideoxy-α-D-glycero-D-galacto-2-nonulopyranoslonate)]oxyacetyl]-L alanine-sodium salt:

Preparation 1:

In 7 ml of a solution comprising tetrahydrofuran:methanol=5:2 was dissolved 150 mg (204 μmole) of the product obtained in Example 8, 1.23 ml (1.23 mmole) of a 1N aqueous NaOH solution was added thereto and the mixture was stirred at room temperature overnight.

The reaction mixture was neutralized by Dowex 50W-X80 and the solvent was distilled to obtain 101 mg of residue.

This product was obtained as 1:1 mixture of Rf=0.056 and 0.042 (objective compound) due to silica gel TLC (chloroform:methanol:acetic acid =5:3:0.5).

Preparation 2:

In 5 ml of tetrahydrofuran was dissolved 200 mg of the product obtained in Example 8, 1.4 ml of a 1N aqueous NaOH solution and the mixture was stirred at room temperature for an hour. Thereafter, 2 ml of water was added thereto and the mixture was further stirred for 30 minutes. The reaction mixture was purified through Sephadex HL-20 (methanol elute) to obtain 261 mg of a product.

This product was obtained as 1:10 mixture of Rf=0.056 and 0.042 (objective substance) due to silica gel TLC (chloroform:methanol:acetic acid=5:3:0.5).

Structural formula

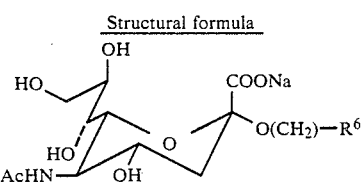

wherein —R⁶ represents

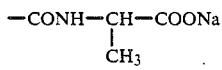

What is claimed is:
1. A sialic acid derivative having an active carbonyl group represented by the formula [I]:

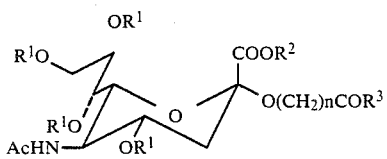

wherein $R^1$ represents hydrogen or acetyl group; $R^2$ represents hydrogen, a metal or a lower alkyl group; $R^3$ represents hydrogen, hydroxyl group, or a residue removed hydrogen from an alcohol portion of an active ester; Ac represents acetyl group; and n is 1 to 20, respectively.

2. The sialic acid derivative havign an active carbonyl group according to claim 1, wherein said compound is represented by the formula [Ia]:

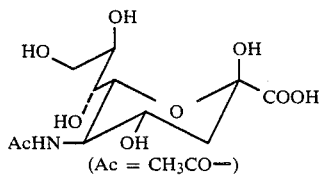

wherein Ac represents acetyl group.

3. The sialic acid derivative having an active carbonyl group according to claim 1, wherein said compound is represented by the formula [Ih]:

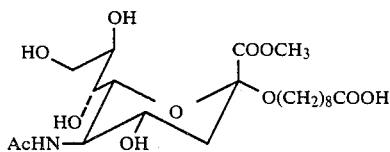

wherein Ac represents acetyl group.

4. The sialic acid derivative having an active carbonyl group according to claim 1, wherein said compound is represented by the formula [Ii]:

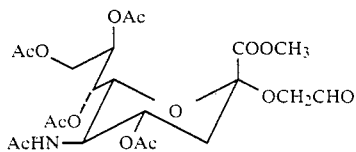

wherein Ac represents acetyl group.

5. The sialic acid derivative having an active carbonyl group according to claim 1, wherein said compound is represented by the formula [Ij]:

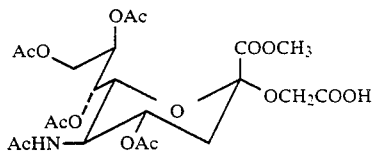

wherein Ac represents acetyl group.

6. The sialic acid derivative having an active carbonyl group according to claim 1, wherein said compound is represented by the formula [Ik]:

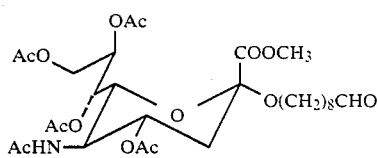

wherein Ac represents acetyl group.

7. The sialic acid derivative having an active carbonyl group according to claim 1, wherein said compound is represented by the formula [Il]:

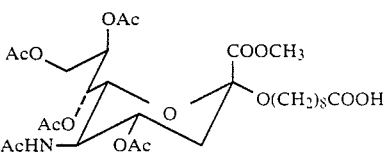

wherein Ac represents acetyl group.

8. The sialic acid derivative having an active carbonyl group according to claim 1, wherein an alcohol portion of an active ester is one selected from the group consisting of N-hydroxysuccinimide, N-hydroxy-5-norbornene-2,3-dicarboximide, N-hydroxyphthalimide, N-hydroxybenzotriazole, p-nitrophenol, 2,4-dinitrophenol, 2,4,5-trichlorophenol and pentachlorophenol.

9. A biological half-life elongating agent of a physiologically active substance comprising a sialic acid derivative having an active carbonyl group represented by the formula [I]:

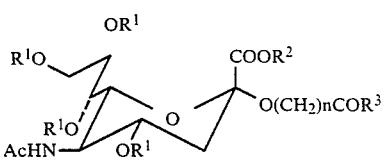

wherein $R^1$ represents hydrogen or acetyl group; $R^2$ represents hydrogen, a metal or a lower alkyl group; $R^3$ represents hydrogen, hydroxyl group, or a residue removed hydrogen from an alcohol portion of an active ester; Ac represents acetyl group; and n is 1 to 20, respectively and suitable physiologically active substance.

10. The biological half-life elongating agent of a physiologically active substance according to claim 9, wherein said compound is represented by the formula [Ih]:

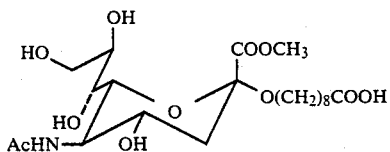

wherein Ac represents acetyl group.

11. The biological half-life elongating agent of a physiologically active substance according to claim 9, wherein said compound is represented by the formula [Ii]:

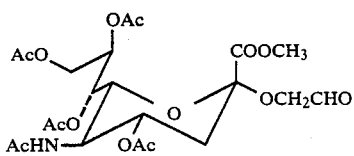

wherein Ac represents acetyl group.

12. The biological half-life elongating agent of a physiologically active substance according to claim 9, wherein said compound is represented by the formula [Ij]:

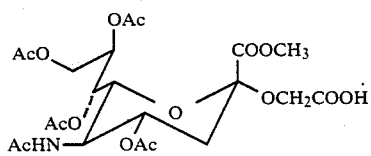

wherein Ac represents acetyl group.

13. The biological half-life elongating agent of a physiologically active substance according to claim 9, wherein said compound is represented by the formula [Ik]:

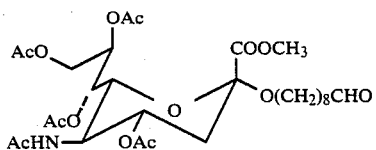

wherein Ac represents acetyl group.

14. The biological half-life elongating agent of a physiologically active substance according to claim 9, wherein said compound is represented by the formula [Il]:

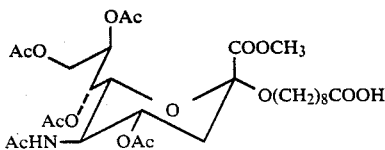

wherein Ac represents acetyl group.

15. The biological half-life elongating agent of a physiologically active substance according to claim 9, wherein said compound is represented by the formula [Im]:

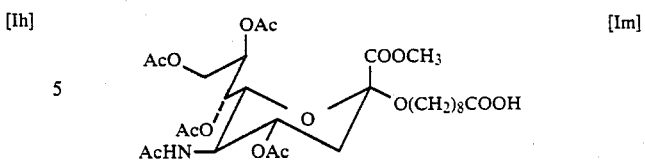

wherein Ac represents acetyl group.

16. The biological half-life elongating agent of a physiologically active substance according to claim 9, wherein an alcohol portion of an active ester is one selected from the group consisting of N-hydroxysuccinimide, N-hydroxy-5-norbornene-2,3-dicarboximide, N-hydroxyphthalimide, N-hydroxybenzotriazole, p-nitrophenol, 2,4-dinitrophenol, 2,4,5-trichlorophenol and pentachlorophenol.

17. A binder of a coupling gel for affinity chromatography comprising a sialic acid derivative having an active carbonyl group represented by the formula [I]:

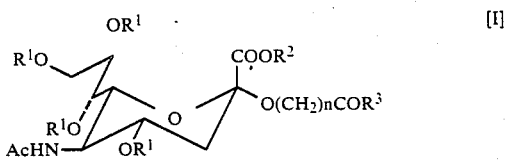

wherein $R^1$ represents hydrogen or acetyl group; $R^2$ represents hydrogen, a metal or a lower alkyl group; $R^3$ represents hydrogen, hydroxyl group, or a residue removed hydrogen from an alcohol portion of an active ester; Ac represents acetyl group; and n is 1 to 20, respectively and a suitable gel support matrix.

18. The binder of a coupling gel for affinity chromatography according to claim 17, wherein said compound is represented by the formula [Ih]:

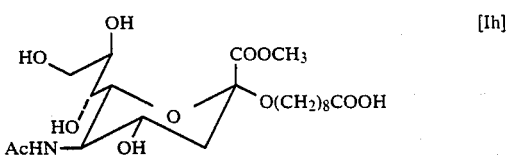

wherein Ac represents acetyl group.

19. The binder of a coupling gel for affinity chromatography according to claim 17, wherein said compound is represented by the formula [Ii]:

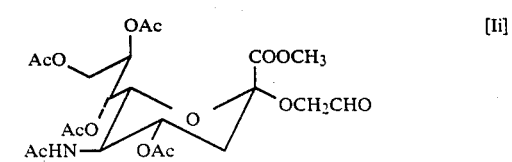

wherein Ac represents acetyl group.

20. The binder of a coupling gel for affinity chromatography according to claim 17, wherein said compound is represented by the formula [Ij]:

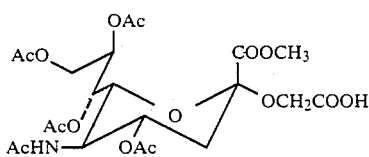

wherein Ac represents acetyl group.

21. The binder of a coupling gel for affinity chromatography according to claim 17, wherein said compound is represented by the formula [Ik]:

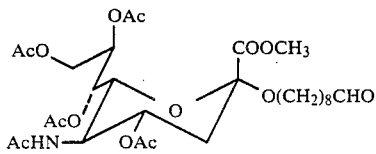

wherein Ac represents acetyl group.

22. The binder of a coupling gel for affinity chromatography according to claim 17, wherein said compound is represented by the formula [Il]:

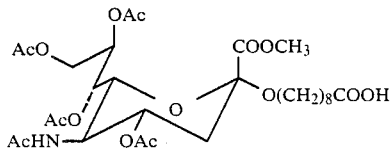

wherein Ac represents acetyl group.

23. The binder of a coupling gel for affinity chromatography according to claim 17, wherein said compound is represented by the formula [Im]:

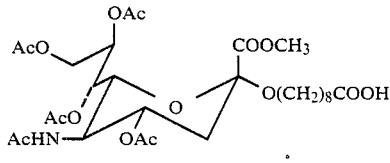

wherein Ac represents acetyl group.

24. The binder of a coupling gel for affinity chromatography according to claim 17, wherein an alcohol portion of an active ester is one selected from the group consisting of N-hydroxysuccinimide, N-hydroxy-5-norbornene-2,3-dicarboximide, N-hydroxyphthalimide, N-hydroxybenzotriazole, p-nitrophenol, 2,4-dinitrophenol, 2,4,5-trichlorophenol and pentachlorophenol.

25. A sialic acid derivative represented by the formula [II]:

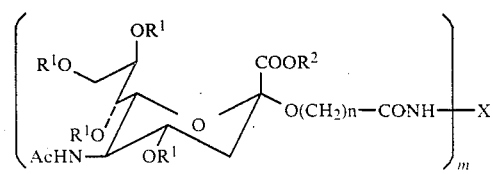

wherein $R^1$ represents hydrogen or acetyl group; $R^2$ represents hydrogen, sodium or a lower alkyl group; Ac represents acetyl group; X represents a residue removed m amino group(s) from an amino compound; m is 1 to 60 and n is 1 to 20, respectively.

26. The sialic acid derivative according to claim 25, wherein X is a residue removed one amino group from an amino acid, or derivative thereof.

27. The sialic acid derivative according to claim 26, wherein said compound is represented by the formula [IIa]:

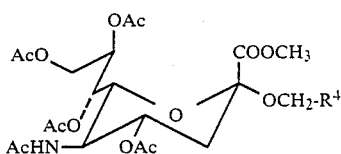

wherein —$R^4$ represents

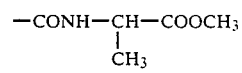

and Ac represents acetyl group, respectively.

28. The sialic acid derivative according to claim 26, wherein said compound is represented by the formula [IIb]:

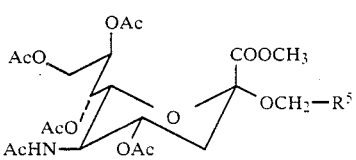

wherein —$R^5$ represents

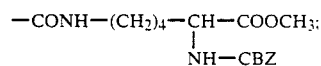

and Ac represents acetyl group, respectively; also, CBZ represents a benzyloxycarbonyl group.

29. The sialic acid derivative according to claim 26, wherein said compound is represented by the formula [IIc]:

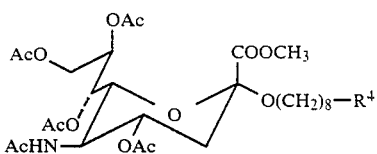

wherein —$R^4$ represents

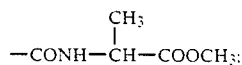

and Ac represents acetyl group, respectively.

30. The sialic acid derivative according to claim 26, wherein said compound is represented by the formula [IId]:

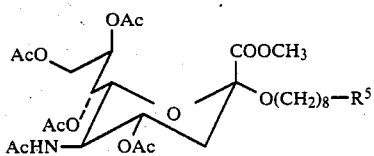

wherein —R⁵ represents

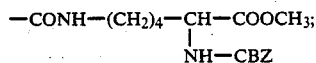

and Ac represents acetyl group, respectively; CBZ represents a benzyloxycarbonyl group.

31. The sialic acid derivative according to claim 26, wherein said compound is represented by the formula [IIe]:

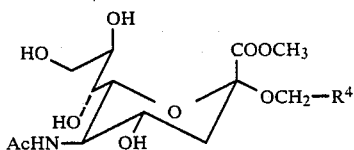

wherein —R⁴ represents

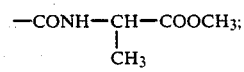

and Ac represents acetyl group, respectively.

32. The sialic acid derivative according to claim 26, wherein said compound is represented by the formula [IIf]:

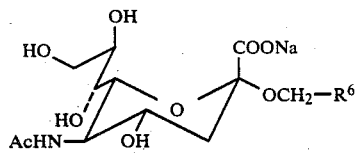

wherein —R⁶ represents

and Ac represents acetyl group, respectively.

33. The sialic acid derivative according to claim 26, wherein X is a residue removed 1 to 60 amino group from peptide or protein, or conjugated protein with which the above and a prosthetic group are combined.

34. The sialic acid derivative according to claim 33, wherein said compound is represented by the formula [IIg]:

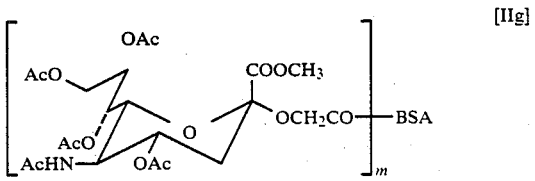

wherein Ac represents acetyl group; and BSA represents Bovine Serum Albumin, respectively.

35. The sialic acid derivative according to claim 33, wherein said compound is represented by the formula [IIh]:

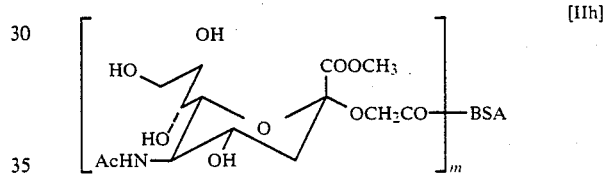

wherein Ac represents acetyl group; and BSA represents Bovine Serum Albumin, respectively.

36. The sialic acid derivative according to claim 33, wherein said compound is represented by the formula [IIi]:

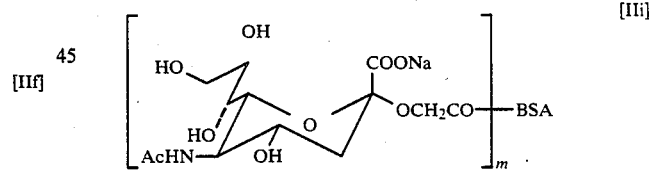

wherein Ac represents acetyl group; and BSA represents Bovine Serum Albumin, respectively.

* * * * *

UNITED STATES PATENT AND TRADEMARK OFFICE
CERTIFICATE OF CORRECTION

PATENT NO. : 4,918,177
DATED : April 17, 1990
INVENTOR(S) : Yoshimura et al.

It is certified that error appears in the above-identified patent and that said Letters Patent is hereby corrected as shown below:

At column 1, line 61, change "snother" to --another--.

At column 2, line 13, change "group(s" to --group(s)--.

At column 2, line 14, delete ")".

At column 3, line 13, change "preferably n is" to --n is preferably--.

At column 4, line 39, after "in" insert --the--.

At column 4, line 42, change "where," to --where--.

At column 4, line 54, change "physilolgically" to --physiologically--.

At column 6, line 22, delete "column" (first occurrence).

At column 12, line 13, change "toluen" to --toluene--.

At column 15, line 56, change "CBz" to --CBZ--.

At column 17, line 56, change "CBz" to --CBZ--.

At column 18, line 43, change "2:1" to --5:1--.

UNITED STATES PATENT AND TRADEMARK OFFICE
CERTIFICATE OF CORRECTION

PATENT NO.   : 4,918,177
DATED        : April 17, 1990
INVENTOR(S)  : Yoshimura et al.

It is certified that error appears in the above-identified patent and that said Letters Patent is hereby corrected as shown below:

At column 22, line 32, change "0.1" to --0.01--.

At column 23, line 33, change "havign" to --having--.
    (claim 2, line 1)

At column 23, lines 36-44, change
    (claim 2, line 4)

"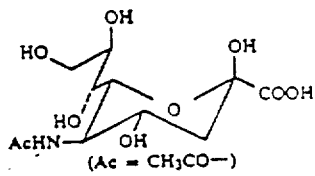"

to

-- 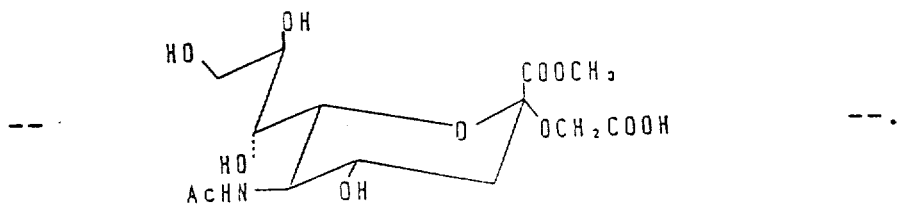 --.

UNITED STATES PATENT AND TRADEMARK OFFICE
CERTIFICATE OF CORRECTION

PATENT NO. : 4,918,177

DATED : April 17, 1990

INVENTOR(S) : Yoshimura et al.

It is certified that error appears in the above-identified patent and that said Letters Patent is hereby corrected as shown below:

At column 25, line 5, change moiety " $-O(CH_2)_8COOH$ " (claim 10, line 5) to $-OCH_2COOH$ --.

At column 25, lines 15-20, change (claim 11, line 5)

"

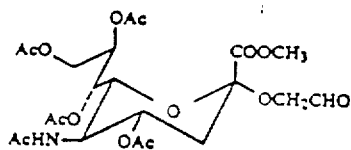

to

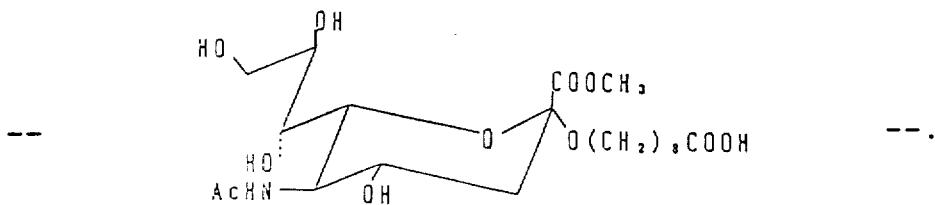

--.

UNITED STATES PATENT AND TRADEMARK OFFICE
CERTIFICATE OF CORRECTION

PATENT NO. : 4,918,177
DATED : April 17, 1990
INVENTOR(S) : Yoshimura et al.

It is certified that error appears in the above-identified patent and that said Letters Patent is hereby corrected as shown below:

At column 25, line 30, change moiety " $-OCH_2COOH$ " to
(claim 12, line 5)
-- $-OCH_2CHO$ --.

At column 25, line 46, change moiety " $-O(CH_2)_8CHO$ " to
(claim 13, line 5)
-- $-OCH_2COOH$ --.

At column 25, line 60, change moiety " $-O(CH_2)_8COOH$ " to
(claim 14, line 6)
-- $-O(CH_2)_8CHO$ --.

At column 26, line 48, change moiety " $-O(CH_2)_8COOH$ " to
(claim 18, line 4)
-- $-OCH_2COOH$ --.

UNITED STATES PATENT AND TRADEMARK OFFICE
CERTIFICATE OF CORRECTION

PATENT NO. : 4,918,177

DATED : April 17, 1990

INVENTOR(S) : Yoshimura et al.

It is certified that error appears in the above-identified patent and that said Letters Patent is hereby corrected as shown below:

At column 26, lines 56-63, change
(claim 19, line 4)

"
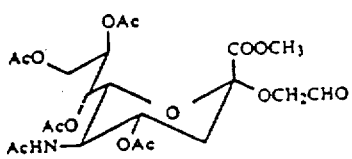
"

to

--
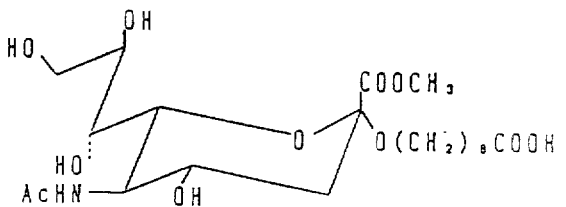
--.

At column 27, line 5, change moiety "-OCH$_2$COOH" to
(claim 20, line 4)
-- -OCH$_2$CHO --.

UNITED STATES PATENT AND TRADEMARK OFFICE
CERTIFICATE OF CORRECTION

PATENT NO. : 4,918,177

DATED : April 17, 1990

INVENTOR(S) : Yoshimura et al.

It is certified that error appears in the above-identified patent and that said Letters Patent is hereby corrected as shown below:

At column 27, line 18, change moiety "$-O(CH_2)_8CHO$" (claim 21, line 4) to $-OCH_2COOH$ --.

At column 27, line 26, change moiety "$-O(CH_2)_8COOH$" (claim 22, line 4) to $-O(CH_2)_8CHO$ --.

Signed and Sealed this

Nineteenth Day of May, 1992

Attest:

DOUGLAS B. COMER

*Attesting Officer*   *Acting Commissioner of Patents and Trademarks*